USO11826143B2

(12) United States Patent
Mortellaro et al.

(10) Patent No.: US 11,826,143 B2
(45) Date of Patent: Nov. 28, 2023

(54) REDUCTION OF IN VIVO ANALYTE SIGNAL DEGRADATION USING MULTIPLE METALS

(71) Applicant: Senseonics, Incorporated, Germantown, MD (US)

(72) Inventors: Mark Mortellaro, Germantown, MD (US); Venkata Velvadapu, Germantown, MD (US); Tina Hyunjung Kim, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 864 days.

(21) Appl. No.: 16/704,220

(22) Filed: Dec. 5, 2019

(65) Prior Publication Data

US 2020/0178854 A1    Jun. 11, 2020

Related U.S. Application Data

(60) Provisional application No. 62/775,634, filed on Dec. 5, 2018.

(51) Int. Cl.
*A61B 5/1455* (2006.01)
*A61B 5/145* (2006.01)
*A61B 5/1473* (2006.01)
*A61B 5/07* (2006.01)

(52) U.S. Cl.
CPC ........ *A61B 5/1455* (2013.01); *A61B 5/14546* (2013.01); *A61B 5/14735* (2013.01); *A61B 5/076* (2013.01); *A61B 5/14503* (2013.01); *A61B 5/14532* (2013.01); *A61B 2562/0233* (2013.01)

(58) Field of Classification Search
CPC .............. A61B 5/1455; A61B 5/14546; A61B 5/14735; A61B 5/14503; A61B 5/076
See application file for complete search history.

(56) References Cited

U.S. PATENT DOCUMENTS

| 5,512,246 A | 4/1996 | Russell et al. |
| 5,517,313 A | 5/1996 | Colvin, Jr. |
| 9,414,775 B2 | 8/2016 | Colvin, Jr. et al. |
| 9,693,714 B2 | 7/2017 | DeHennis et al. |
| 9,931,068 B2 | 4/2018 | Huffstetler et al. |
| 2002/0032374 A1 | 3/2002 | Holker et al. |
| 2011/0295128 A1 | 12/2011 | Yuasa et al. |

(Continued)

FOREIGN PATENT DOCUMENTS

| CN | 105530867 A | 4/2016 |
| WO | 2011/097586 A1 | 8/2011 |

*Primary Examiner* — Marjan Fardanesh
(74) *Attorney, Agent, or Firm* — Rothwell, Figg, Ernst & Manbeck, P.C.

(57) ABSTRACT

A sensor (e.g., an optical sensor) that may be implanted within a living animal (e.g., a human) and may be used to measure an analyte (e.g., glucose or oxygen) in a medium (e.g., interstitial fluid, blood, or intraperitoneal fluid) within the animal. The sensor may include a sensor housing, an analyte indicator covering at least a portion of the sensor housing, and a multiple metal protective system including multiple metals incorporated in and/or in close proximity to a surface of the analyte indicator that reduce deterioration of the analyte indicator.

15 Claims, 8 Drawing Sheets

(56) References Cited

U.S. PATENT DOCUMENTS

| | | | |
|---|---|---|---|
| 2012/0238842 A1* | 9/2012 | Colvin, Jr. | A61B 5/145 |
| | | | 600/300 |
| 2013/0241745 A1 | 9/2013 | Colvin, Jr. et al. | |
| 2013/0243656 A1 | 9/2013 | Chan et al. | |
| 2014/0187877 A1 | 7/2014 | Emken et al. | |
| 2015/0057509 A1 | 2/2015 | Huffstetler et al. | |
| 2017/0202517 A1 | 7/2017 | Colvin, Jr. et al. | |
| 2018/0192926 A1 | 7/2018 | Shults et al. | |
| 2018/0220940 A1 | 8/2018 | Huffstetler et al. | |

* cited by examiner

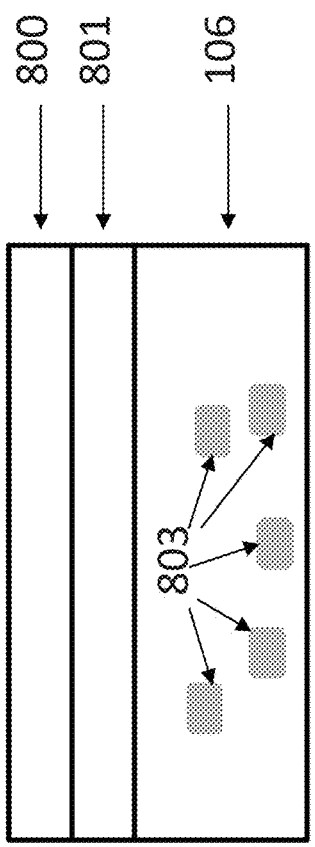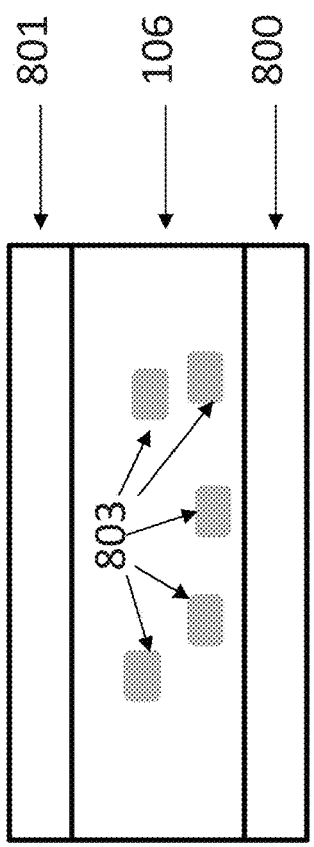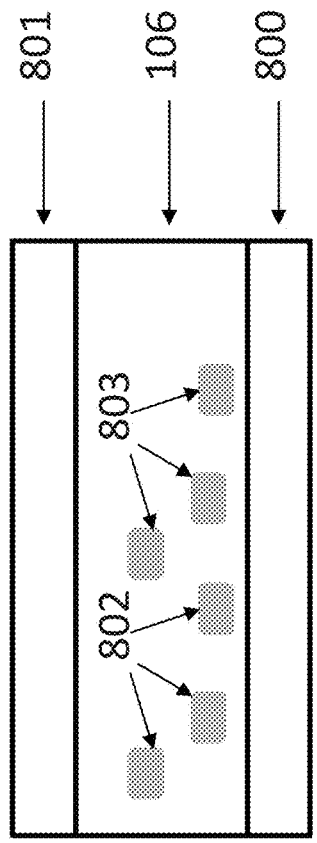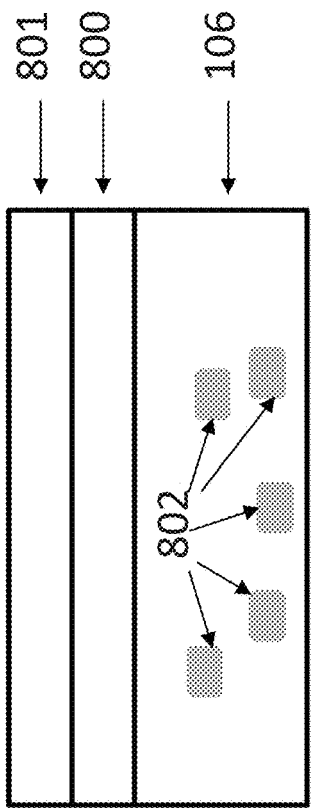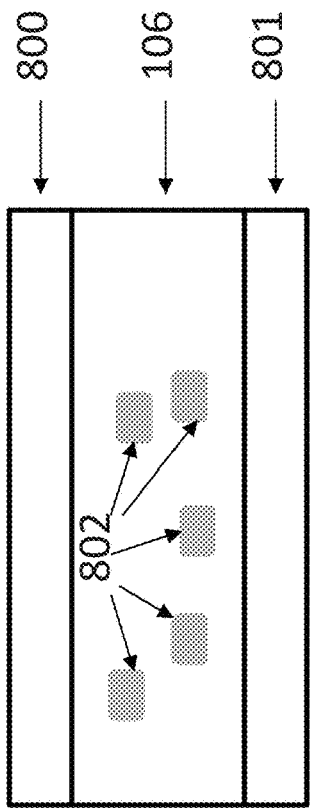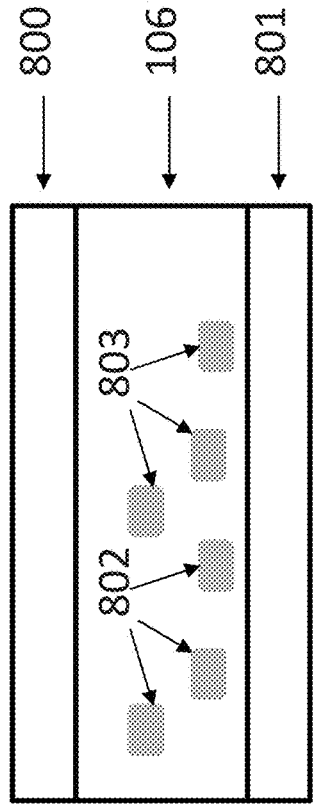

REDUCTION OF IN VIVO ANALYTE SIGNAL DEGRADATION USING MULTIPLE METALS

CROSS-REFERENCE TO RELATED APPLICATION

The present application claims the benefit of priority to U.S. Provisional Application Ser. No. 62/775,634, filed on Dec. 5, 2018, which is incorporated herein by reference in its entirety.

BACKGROUND

Field of Invention

The present invention relates generally to catalytic protection of materials from in vivo degradation when measuring an analyte in a medium of a living animal using a system including a sensor implanted (partially or fully) or inserted into the living animal. Specifically, the present invention relates to a sensor that utilizes multiple metals, which may be collectively or independently incorporated within an analyte indicator, formed on one or more surfaces of an analyte indicator, and/or stacked on at least a portion of a surface of the analyte indicator (e.g., one metal layer on top of another metal layer).

Discussion of the Background

A sensor may be implanted (partially or fully) within a living animal (e.g., a human) and used to measure an analyte (e.g., glucose, oxygen, cardiac markers, low-density lipoprotein (LDL), high-density lipoprotein (HDL), or triglycerides) in a medium (e.g., interstitial fluid (ISF), blood, or intraperitoneal fluid) within the living animal. The sensor may include a light source (e.g., a light-emitting diode (LED) or other light emitting element), indicator molecules, and a photodetector (e.g., a photodiode, phototransistor, photoresistor or other photosensitive element). Examples of implantable sensors employing indicator molecules to measure an analyte are described in U.S. Pat. Nos. 5,517,313 and 5,512,246, which are incorporated herein by reference in their entirety.

A sensor may include an analyte indicator, which may be in the form of indicator molecules embedded in a graft (i.e., layer or matrix). For example, in an implantable fluorescence-based glucose sensor, fluorescent indicator molecules may reversibly bind glucose and, when irradiated with excitation light (e.g., light having a wavelength of approximately 378 nm), emit an amount of light (e.g., light in the range of 400 to 500 nm) that depends on whether glucose is bound to the indicator molecule.

If a sensor is implanted in the body of a living animal, the animal's immune system may begin to attack the sensor. For instance, if a sensor is implanted in a human, white blood cells may attack the sensor as a foreign body, and, in the initial immune system onslaught, neutrophils may be the primary white blood cells attacking the sensor. The defense mechanism of neutrophils includes the release of highly caustic substances known as reactive oxygen species. The reactive oxygen species include, for example, hydrogen peroxide.

Hydrogen peroxide and other reactive species such as reactive oxygen and nitrogen species may degrade the indicator molecules of an analyte indicator. For instance, in indicator molecules having a boronate group, hydrogen peroxide may degrade the indicator molecules by oxidizing the boronate group, thus disabling the ability of the indicator molecule to bind glucose.

There is presently a need in the art for improvements in protecting analyte indicator from degradation. There is also a need in the art for continuous analyte sensors having increased longevity.

SUMMARY

The present invention overcomes the disadvantages of prior systems by providing, among other advantages, reduced analyte indicator degradation.

In one aspect, the present invention may provide a device having a partially or fully implantable device which has in vivo functionality, as well as a protective material in close proximity to the surface of the implantable device. The protective material may prevent or reduce degradation or interference of the implantable device due to inflammation reactions and/or foreign body response. Further, the protective material can include metals, metal complexes, or metal oxides which catalytically decompose or inactivate in vivo reactive species or biological oxidizers. As used herein, the term "metal" includes metal alloys, metal complexes, and metal oxides.

In one aspect, the protective material may be covering, provided on, incorporated with and/or suspended within the external structure of the implantable device.

One aspect of the present invention provides a sensor for measurement of an analyte in a medium within a living animal. The sensor may include a sensor housing, an analyte indicator covering at least a portion of the sensor housing, and a protective system including multiple metals incorporated in and/or in close proximity to a surface of the analyte indicator, and the multiple metals may be configured to reduce deterioration of the analyte indicator. In one aspect, the sensor may include a protective system having a metal layer including one or more of the multiple metals. In one aspect, the sensor may have metal layer covering at least a portion of the analyte indicator.

In one aspect, the sensor may have a first metal layer and a second metal layer, the first metal layer including a first metal of the multiple metals, the second metal layer may include a second metal of the multiple metals, and the first and second metals are different metals. The first metal layer may cover at least a portion of the analyte indicator. The second metal layer may cover at least a portion of the first metal layer. In one aspect, the second metal layer may be capable of adhering to the first metal layer better than the second metal layer is capable of adhering to the analyte indicator. In one aspect, the second metal layer may be between at least a portion of the sensor housing and the analyte indicator, and the first metal layer may cover at least a portion of the analyte indicator that is distal to the sensor housing. In one aspect, the first metal layer may be between at least a portion of the sensor housing and the analyte indicator, and the second metal layer may cover at least a portion of the analyte indicator that is distal to the sensor housing.

In one aspect, the protective system may include metal particles incorporated within the analyte indicator, and the metal particles may include one or more of the multiple metals. In some aspects, the metal particles may include a first metal and a second metal, and the first and second metals are different metals. In one aspect, the metal layer may be a multi-metal layer that includes a first metal of the multiple metals and a second metal of the multiple metals, and the first and second metals are different metals.

In one aspect, the protective system may include multiple metals that are configured to collectively interact or react with multiple degradative species. In some aspects, the multiple metals of the protective system may be configured to collectively interact or react with at least two of hydrogen peroxide, a reactive oxygen species, enzymes, metal ions, a reactive nitrogen species, and a free radical.

In some aspects, the multiple metals of the protective system may be configured to inhibit oxidative properties of the degradative species. In some aspects, the multiple metals of the protective system may include a first metal selected from Cu, W, Pt, Fe, Mo, oxides, alloys, and complexes thereof and a second metal selected from Mo, W, Cu, Fe, and Co, oxides, alloys, and complexes thereof, and the first metal and the second metal are different from each other.

In some aspects, the sensor may further include a radiation source contained in said sensor body and configured to emit radiation to the indicator element. In some aspects, the sensor may further include a photosensitive element contained in the sensor body and configured to receive light emitted by the analyte indicator. In some aspects, the sensor may further include a carrier material covering at least a portion of the analyte indicator, wherein multiple metals are incorporated within the material.

In some aspects, the present disclosure includes a method for detecting the presence or concentration of an analyte in an in vivo sample including the steps of exposing the in vivo sample to a device having a detectable quality that changes when the device is exposed to an analyte of interest, wherein the device may include protective material that prevents or reduces degradation or interference of the device from degradative species or biological oxidizers, and wherein the device may include a sensor of the present disclosure; and measuring a change in the detectable quality to thereby detect the presence or concentration of an analyte of interest in the in vivo sample.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 7A and 7B are schematic views illustrating an analyte indicator, protective layers, and a protective material embodying aspects of the present invention.

FIGS. 8A and 8B are schematic views illustrating an analyte indicator, protective layers, and a protective material embodying aspects of the present invention.

FIGS. 9A and 9B are schematic views illustrating analyte indicator, protective layers, and protective materials embodying aspects of the present invention.

DETAILED DESCRIPTION OF PREFERRED EMBODIMENTS

Figure 1:
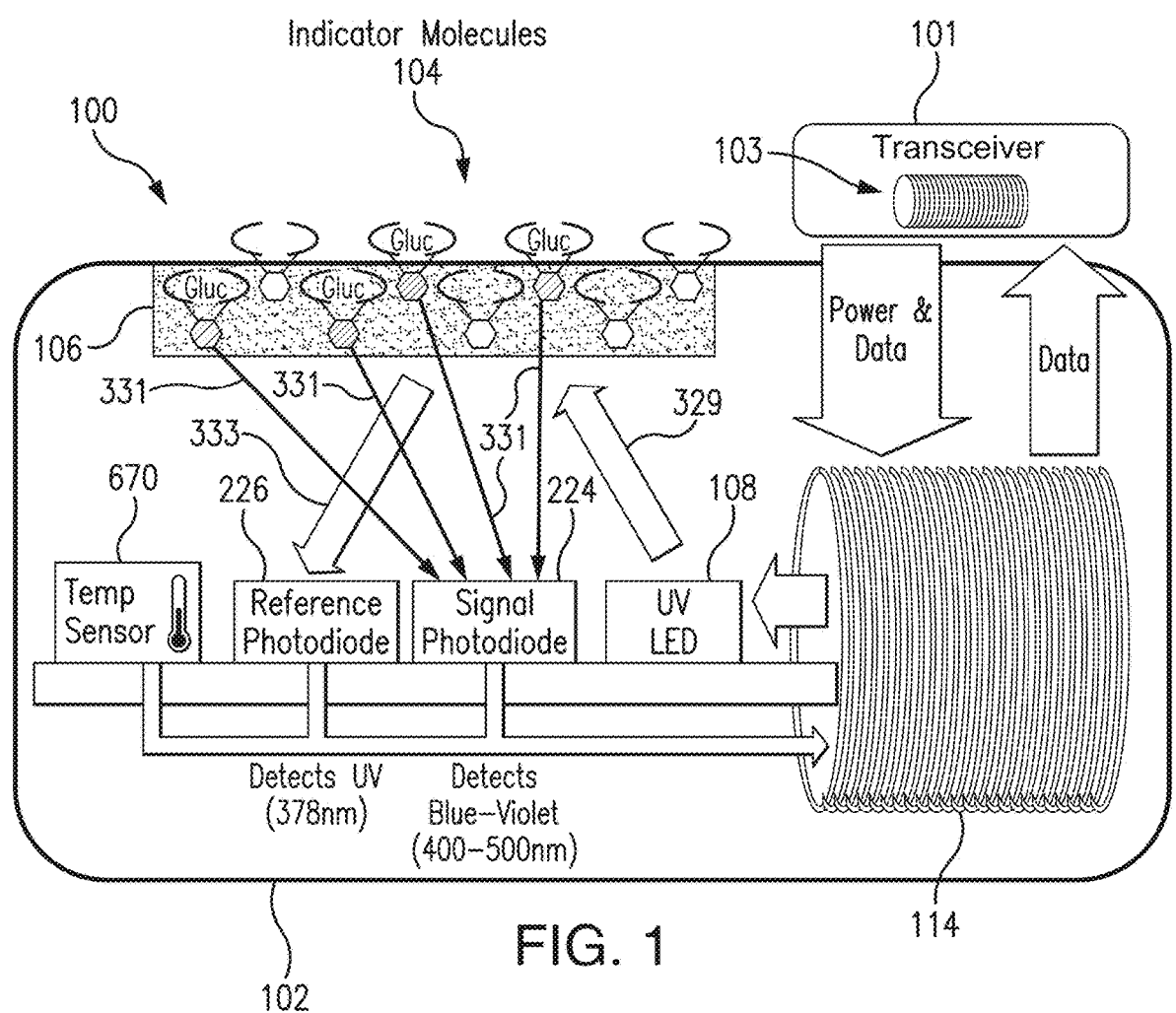
FIG. 1 is a schematic view illustrating a sensor system embodying aspects of the present invention.

In some embodiments, the present invention includes a sensor device that may be for implantation or insertion within a living animal and measurement of an analyte in a medium within the living animal. The sensor device may include a sensor housing, an analyte indicator covering at least a portion of the sensor housing, and at least one multi-metal material that reduces deterioration of the analyte indicator.

In some embodiments, the sensor device may include at least one multi-metal material covering at least a portion of an analyte indicator that is provided on a sensor housing.

In some embodiments, the sensor device may include a sensor housing having an analyte indicator covering at least a portion of a surface of the sensor housing, a first single- or multi-metal material or layer covering at least a portion of the analyte indicator, and a second single- or multi-metal material or layer covering at least a portion of the first single- or multi-metal layer.

In some embodiments, the sensor device may include a sensor housing having an analyte indicator covering at least a portion of a surface of the sensor housing, a first single- or multi-metal material or layer provided between at least a portion of the sensor housing and the analyte indicator, and a second single- or multi-metal material or layer covering at least a portion of the analyte indicator that is distal to the sensor housing.

In some embodiments, the sensor device may include a sensor housing having an analyte indicator covering at least a portion of a surface of the sensor housing, at least one metal incorporated within the analyte indicator and at least one single- or multi-metal material or layer covering at least a portion of an analyte indicator distal to the sensor housing.

In another aspect, the present invention relates to a method for using an implantable device in in vivo applications. The method includes at least providing an implantable device which has an in vivo functionality. The implantable device has a protective material applied onto the device, wherein the protective material applied by the method prevents or reduces degradation or interference of the implantable device due to inflammation reactions and/or foreign body response. The protective material applied by the method includes multiple metals (including metal complexes and metal oxides) which catalytically decompose or inactivate multiple different in vivo degradative species or biological oxidizers. As used herein, the terms "degradative species" and "biological oxidizers" generally refer to reactive physiological molecules and radicals that degrade the indicator molecules. The method further includes partially or fully implanting the implantable device in a subject body.

In another aspect, the present invention relates to a method for detecting the presence or concentration of an analyte in an in vivo sample. The method includes at least exposing the in vivo sample to a device having a detectable quality that changes when the device is exposed to an analyte of interest. The device includes in part protective material, wherein the protective material prevents or reduces degradation or interference of the device from degradative species or biological oxidizers. The method further includes measuring any change in the detectable quality to thereby determine the presence or concentration of an analyte of interest in the in vivo sample.

In another aspect, the present invention is an implantable glucose sensor for determining the presence or concentration of glucose in an animal. The sensor device can include a sensor body having an outer surface surrounding the sensor body, a radiation source in said sensor body which emits radiation within said sensor body, an indicator element that is affected by the presence or concentration of glucose in said animal, where the indicator element having indicator molecules is positioned in close proximity to at least a portion of the outer surface of the sensor body. Further, the sensor can include a photosensitive element located in the sensor body, positioned to receive radiation within the sensor body, where the photosensitive element is configured to emit a signal responsive to radiation received from an indicator element and which is indicative of the presence or concentration of glucose in an animal. Moreover, the sensor includes a protective material that protects the indicator molecules from degradative species or biological oxidizers.

FIG. 1 is a schematic view of a sensor system embodying aspects of the present invention. In some non-limiting embodiment, as shown in FIG. 1, the system may include a sensor 100 and an external transceiver 101. In some embodiments, the sensor 100 may be an implantable sensor configured to be fully or partially implanted in a living animal (e.g., a living human). The sensor 100 may be implanted, for example, in a living animal's arm, wrist, leg, abdomen, peritoneum, or other region of the living animal suitable for sensor implantation. For example, in some non-limiting embodiments, the sensor 100 may be implanted beneath the skin (i.e., in the subcutaneous or peritoneal tissues). However, this is not required, and, in some alternative embodiments, the sensor 100 may be a transcutaneous sensor.

In some embodiments, a transceiver 101 may be an electronic device that communicates with the sensor 100 to power the sensor 100, provide commands and/or data to the sensor 100, and/or receive data from the sensor 100. In some embodiments, the received data may include one or more sensor measurements. In some embodiments, the sensor measurements may include, for example and without limitation, one or more light measurements from one or more photodetectors of the sensor 100 and/or one or more temperature measurements from one or more temperature sensors of the sensor 100. In some embodiments, the transceiver 101 may calculate analyte (e.g., glucose) concentrations from the measurement information received from the sensor 100.

In some non-limiting embodiments, the transceiver 101 may be a handheld device or an on-body/wearable device. For example, in some embodiments where the transceiver 101 is an on-body/wearable device, the transceiver 101 may be held in place by a band (e.g., an armband or wristband) and/or adhesive, and the transceiver 101 may convey (e.g., periodically, such as every two minutes, and/or upon user initiation) measurement commands (i.e., requests for measurement information) to the sensor 100. In some embodiments where the transceiver 101 is a handheld device, positioning (i.e., hovering or swiping/waving/passing) the transceiver 101 within range over the sensor implant site (i.e., within proximity of the sensor 100) may cause the transceiver 101 to automatically convey a measurement command to the sensor 100 and receive a data from the sensor 100.

In some embodiments, as shown in FIG. 1, the transceiver 101 may include an inductive element 103, such as, for example, a coil. In some embodiments, the transceiver 101 may generate an electromagnetic wave or electrodynamic field (e.g., by using a coil) to induce a current in an inductive element 114 of the sensor 100. In some non-limiting embodiments, the sensor 100 may use the current induced in the inductive element 114 to power the sensor 100. However, this is not required, and, in some alternative embodiments, the sensor 100 may be powered by an internal power source (e.g., a battery).

In some embodiments, the transceiver 101 may convey data (e.g., commands) to the sensor 100. For example, in some non-limiting embodiments, the transceiver 101 may convey data by modulating the electromagnetic wave generated by the inductive element 103 (e.g., by modulating the current flowing through the inductive element 103 of the transceiver 101). In some embodiments, the sensor 100 may detect/extract the modulation in the electromagnetic wave generated by the transceiver 101. Moreover, the transceiver 101 may receive data (e.g., one or more sensor measurements) from the sensor 100. For example, in some non-limiting embodiments, the transceiver 101 may receive data by detecting modulations in the electromagnetic wave generated by the sensor 100, e.g., by detecting modulations in the current flowing through the inductive element 103 of the transceiver 101.

In some embodiments, as shown in FIG. 1, the sensor 100 may include a sensor housing 102 (i.e., body, shell, capsule, or encasement), which may be rigid and biocompatible. In exemplary embodiments, sensor housing 102 may be formed from a suitable, optically transmissive polymer material, such as, for example, acrylic polymers (e.g., polymethylmethacrylate (PMMA)).

In some embodiments, as shown in FIG. 1, the sensor 100 may include an analyte indicator 106. In some non-limiting embodiments, the analyte indicator 106 may be a polymer graft coated, diffused, adhered, or embedded on at least a portion of the exterior surface of the sensor housing 102. The analyte indicator 106 (e.g., polymer graft) may cover the entire surface of sensor housing 102 or only one or more portions of the surface of housing 102. As an alternative to coating the analyte indicator 106 on the outer surface of sensor housing 102, the analyte indicator 106 may be disposed on the outer surface of the sensor housing 102 in other ways, such as by deposition or adhesion. In some embodiments, the analyte indicator 106 may be a fluorescent glucose indicating polymer. In one non-limiting embodiment, the polymer is biocompatible and stable, grafted onto the surface of sensor housing 102, designed to allow for the direct measurement of glucose in interstitial fluid (ISF), blood, or intraperitoneal fluid after implantation of the sensor 100. In some embodiments, the analyte indicator 106 may be a hydrogel.

In some embodiments, the analyte indicator 106 (e.g., polymer graft) of the sensor 100 may include indicator molecules 104. The indicator molecules 104 may be distributed throughout the entire analyte indicator 106 or only throughout one or more portions of the analyte indicator 106. The indicator molecules 104 may be fluorescent indicator molecules (e.g., TFM having the chemical name 9-[N-[6-(4,4,5,5,-tetramethyl-1,3,2-dioxaborolano)-3-(trifluoromethyl)benzyl]-N-[3-(methacrylamido)propylamino]methyl]-10-[N-[6-(4,4,5,5,-tetramethyl-1,3,2-dioxaborolano)-3-(trifluoromethyl)benzyl]-N-[2-(carboxyethyl)amino]methyl]anthracene sodium salt) or light absorbing, non-fluorescent indicator molecules. In some embodiments, the indicator molecules 104 may reversibly bind an analyte (e.g., glucose, oxygen, cardiac markers, low-density lipoprotein (LDL), high-density lipoprotein (HDL), or triglycerides). When an indicator molecule 104 has bound an analyte, the indicator molecule may become fluorescent, in which case the indicator molecule 104 is capable of absorbing (or being excited by) excitation light 329 and emitting light 331. In one non-limiting embodiment, the excitation light 329 may have a wavelength of approximately 378 nm, and the emission light 331 may have a wavelength in the range of 400 to 500 nm. When no analyte is bound, the indicator molecule 104 may be only weakly fluorescent.

In some embodiments, the sensor 100 may include a light source 108, which may be, for example, a light emitting diode (LED) or other light source that emits radiation, including radiation over a range of wavelengths that interact with the indicator molecules 104. In other words, the light source 108 may emit the excitation light 329 that is absorbed by the indicator molecules in the matrix layer/polymer 104. As noted above, in one non-limiting embodiment, the light source 108 may emit excitation light 329 at a wavelength of approximately 378 nm.

In some embodiments, the sensor 100 may also include one or more photodetectors (e.g., photodiodes, phototransistors, photoresistors or other photosensitive elements). For example, in the embodiment illustrated in FIG. 1, sensor 100 has a first photodetector 224 and a second photodetector 226. However, this is not required, and, in some alternative embodiments, the sensor 100 may only include the first photodetector 224. In the case of a fluorescence-based sensor, the one or more photodetectors may be sensitive to fluorescent light emitted by the indicator molecules 104 such that a signal is generated by a photodetector (e.g., photodetector 224) in response thereto that is indicative of the level of fluorescence of the indicator molecules and, thus, the amount of analyte of interest (e.g., glucose).

Some part of the excitation light 329 emitted by the light source 108 may be reflected from the analyte indicator 106 back into the sensor 100 as reflection light 333, and some part of the absorbed excitation light may be emitted as emitted (fluoresced) light 331. In one non-limiting embodiment, the emitted light 331 may have a different wavelength than the wavelength of the excitation light 329. The reflected light 333 and emitted (fluoresced) light 331 may be absorbed by the one or more photodetectors (e.g., first and second photodetectors 224 and 226) within the body of the sensor 100.

Each of the one or more photodetectors may be covered by a filter 112 (see FIG. 3) that allows only a certain subset of wavelengths of light to pass through. In some embodiments, the one or more filters 112 may be thin glass filters. In some embodiments, the one or more filters 112 may be thin film (e.g., dichroic) filters deposited on the glass and may pass only a narrow band of wavelengths and otherwise reflect most of the received light. In some embodiments, the filters may be thin film (dichroic) filters deposited directly onto the photo detectors and may pass only a narrow band of wavelengths and otherwise reflect most of the light received thereby. The filters 112 may be identical (e.g., both filters 112 may allow signals to pass) or different (e.g., one filter 112 may be a reference filter and another filter 112 may be a signal filter).

In one non-limiting embodiment, the second (reference) photodetector 226 may be covered by a reference photodiode filter that passes light at the same wavelength as is emitted from the light source 108 (e.g., 378 nm). The first (signal) photodetector 224 may detect the amount of fluoresced light 331 that is emitted from the molecules 104 in the analyte indicator 106. In one non-limiting embodiment, the peak emission of the indicator molecules 104 may occur around 435 nm, and the first photodetector 224 may be covered by a signal filter that passes light in the range of about 400 nm to 500 nm. In some embodiments, higher glucose levels/concentrations correspond to a greater amount of fluorescence of the molecules 104 in the analyte indicator 106, and, therefore, a greater number of photons striking the first photodetector 224.

In some embodiments, as shown in FIG. 1, the sensor 100 may include a substrate 116. In some embodiments, the substrate 116 may be a circuit board (e.g., a printed circuit board (PCB) or flexible PCB) on which circuit components (e.g., analog and/or digital circuit components) may be mounted or otherwise attached. However, in some alternative embodiments, the substrate 116 may be a semiconductor substrate having circuitry fabricated therein. The circuitry may include analog and/or digital circuitry. Also, in some semiconductor substrate embodiments, in addition to the circuitry fabricated in the semiconductor substrate, circuitry may be mounted or otherwise attached to the semiconductor substrate 116. In other words, in some semiconductor substrate embodiments, a portion or all of the circuitry, which may include discrete circuit elements, an integrated circuit (e.g., an application specific integrated circuit (ASIC)) and/or other electronic components, may be fabricated in the semiconductor substrate 116 with the remainder of the circuitry is secured to the semiconductor substrate 116, which may provide communication paths between the various secured components.

In some embodiments, the one or more of the sensor housing 102, analyte indicator 106, indicator molecules 104, light source 108, photodetectors 224, 226, temperature transducer 670, substrate 116, and inductive element 114 of sensor 100 may include some or all of the features described in one or more of U.S. application Ser. No. 13/761,839, filed on Feb. 7, 2013, U.S. application Ser. No. 13/937,871, filed on Jul. 9, 2013, and U.S. application Ser. No. 13/650,016, filed on Oct. 11, 2012, all of which are incorporated by reference in their entireties. Similarly, the structure and/or function of the sensor 100 and/or transceiver 101 may be as described in one or more of U.S. application Ser. Nos. 13/761,839, 13/937,871, and 13/650,016, which are incorporated herein by reference in their entireties.

In some embodiments, the sensor 100 may include a transceiver interface device, and the transceiver 101 may include a sensor interface device. In some embodiments where the sensor 100 and transceiver 101 include an antenna or antennas (e.g., inductive elements 103 and 114), the transceiver interface device may include the inductive element 114 of the sensor 100, and the sensor interface device may include the inductive element 103 of the transceiver 101. In some of the transcutaneous embodiments where there exists a wired connection between the sensor 100 and the transceiver 101, the transceiver interface device and sensor interface device may include the wired connection.

Figure 2:
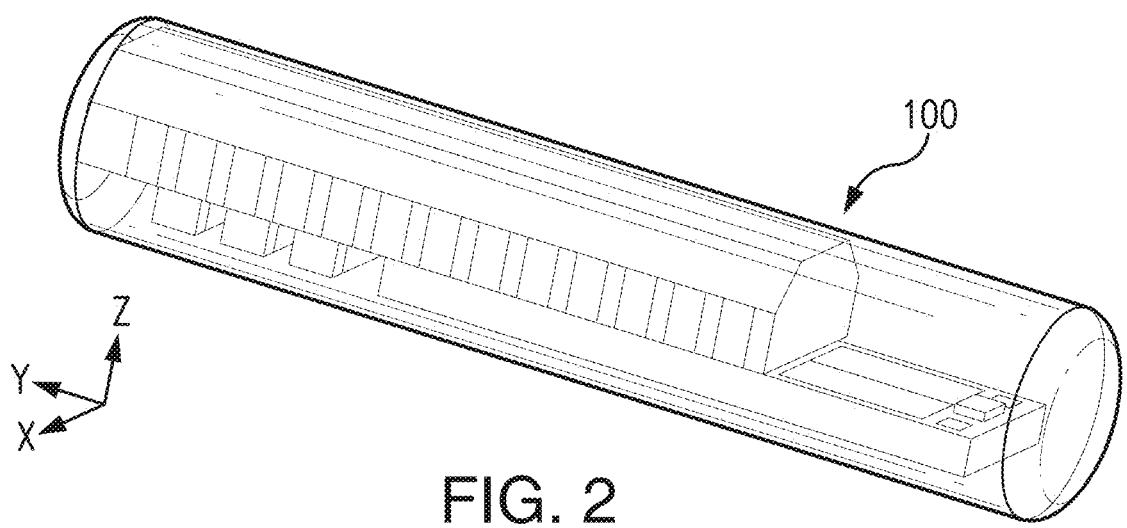
FIG. 2 illustrates a perspective view of a sensor embodying aspects of the present invention.
Figure 3:
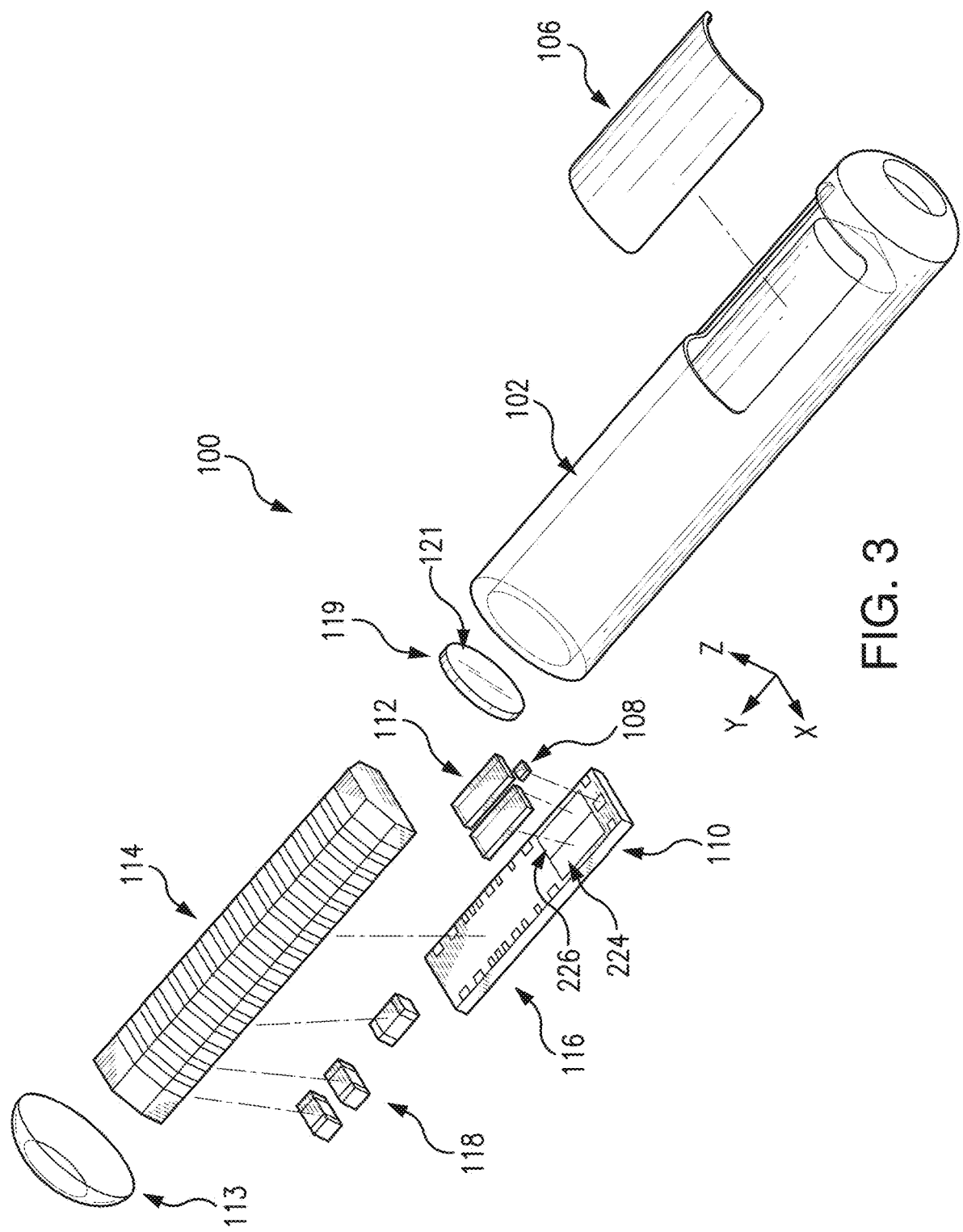
FIG. 3 illustrates an exploded view of a sensor embodying aspects of the present invention.

FIGS. 2 and 3 illustrate a non-limiting embodiment of a sensor 100 embodying aspects of the present invention that may be used in the sensor system illustrated in FIG. 1. FIGS. 2 and 3 illustrate perspective and exploded views, respectively, of the non-limiting embodiment of the sensor 100.

In some embodiments, as illustrated in FIG. 3, the sensor housing 102 may include an end cap 113. In some embodiments, the sensor 100 may include one or more capacitors 118. The one or more capacitors 118 may be, for example, one or more tuning capacitors and/or one or more regulation capacitors. The one or more capacitors 118 may be too large for fabrication in the semiconductor substrate 116 to be practical. Further, the one or more capacitors 118 may be in addition to one or more capacitors fabricated in the semiconductor substrate 116.

In some embodiments, as illustrated in FIG. 3, the sensor 100 may include a reflector 119 (i.e., mirror). Reflector 119 may be attached to the semiconductor substrate 116 at an end thereof. In a non-limiting embodiment, reflector 119 may be attached to the semiconductor substrate 116 so that a face portion 121 of reflector 119 is generally perpendicular to a top side of the semiconductor substrate 116 (i.e., the side of semiconductor substrate 116 on or in which the light source 108 and one or more photodetectors 110 are mounted or fabricated) and faces the light source 108. The face 121 of the reflector 119 may reflect radiation emitted by light source 108. In other words, the reflector 119 may block radiation emitted by light source 108 from exiting the axial end of the sensor 100.

According to one aspect of the invention, an application for which the sensor 100 was developed (although by no means the only application for which it is suitable) is measuring various biological analytes in the living body of an animal (including a human). For example, sensor 100 may be used to measure glucose, oxygen, toxins, pharmaceuticals or other drugs, hormones, and other metabolic analytes in, for example, the human body.

In some embodiments, the specific composition of the analyte indicator 106 and the indicator molecules 104 may vary depending on the particular analyte the sensor is to be used to detect and/or where the sensor is to be used to detect the analyte (e.g., in the in subcutaneous tissues, blood, or peritoneum). In some embodiments, the analyte indicator 106 facilitates exposure of the indicator molecules 104 to the analyte. In some embodiments, the indicator molecules 104 may exhibit a characteristic (e.g., emit an amount of fluorescence light) that is a function of the concentration of the specific analyte to which the indicator molecules 104 are exposed.

In some embodiments, the sensor 100 may include at least one drug eluting polymer matrix and/or a layer of catalyst and/or one or more therapeutic agents that may be provided on, incorporated in, or dispersed within the analyte indicator or sensor housing as described in U.S. Pat. No. 9,931,068 (Huffstetler et al.), which is incorporated herein by reference in its entirety. In some embodiments, the one or more therapeutic agents may be incorporated in the analyte indicator 106. In some embodiments, the sensor 100 may include a membrane covering at least a portion of the analyte indicator 106, and the one or more therapeutic agents may be incorporated within the membrane. In some embodiments, the one or more therapeutic agents include dexamethasone, triamcinolone, betamethasone, methylprednisolone, beclometasone, fludrocortisone, derivatives thereof, and analogs thereof, a glucocorticoid, an anti-inflammatory drug, e.g., a non-steroidal anti-inflammatory drug including but not limited to acetylsalicylic acid, isobutylphenylpropanoic acid.

The implantation or insertion of a medical device, such as a bio-sensor, into a user/patient's body can cause the body to exhibit adverse physiological reactions that are detrimental to the functioning of the device. The reactions may range from infections due to implantation surgery to the immunological response of a foreign object implanted in the body. That is, the performance of the implantable bio-sensor can be hindered or permanently damaged in vivo via the immunological response to an infection or the device itself. In particular, the performance of the analyte indicator 106 may be deteriorated by the immunological response of the body into which the sensor 100 is implanted. For example, as explained above, white blood cells, including neutrophils, may attack an implanted sensor 100. The neutrophils release, inter alia, hydrogen peroxide, which may degrade indicator molecules 104 (e.g., by oxidizing a boronate group of an indicator molecule 104 and disabling the ability of the indicator molecule 104 to bind glucose and/or fluoresce).

In some embodiments, the analyte indicator 106 may be protected by multiple metals (including metal alloys, metal complexes, or metal oxides) that interact or react with one or more degradative species without compromising signal integrity or performance of the sensor device. In some embodiments, one or more metals may be incorporated into the analyte indicator 106 that may cover at least a portion of the sensor housing 102. In some embodiments, one or more metal layers may be additionally or alternatively applied to the analyte indicator 106. In some embodiments, the degradative species may include one or more of hydrogen peroxide, enzymes, metal ions, a reactive oxygen species, a reactive nitrogen species, and a free radical.

In some embodiments, one or more metals may be incorporated into the analyte indicator 106 that may cover at least a portion of the sensor housing 102. In some embodiments, one or more metals may additionally or alternatively cover at least a portion of the surface of the analyte indicator 106 that is distal to a portion of the sensor housing 102. In some embodiments, one or more metals may additionally or alternatively cover at least a portion of the surface of the analyte indicator 106 that is proximal to the sensor housing 102. In some embodiments, a layer covering at least a portion of the analyte indicator 106 may include at least two different metal species, and surfaces of each of the at least two different metal species may be exposed to degradative species or biological oxidizers.

While a platinum layer has been clinically demonstrated to improve in vivo longevity of the Senseonics implanted CGM sensors (Colvin A E, Jiang H. 2012 Increased in vivo stability and functional lifetime of an implantable glucose sensor through platinum catalysis. J Biomed Mater Res Part A 2013 May; 101(5):1274-82), increasing the surface area (and therefore amount of catalyst) of the platinum layer may not further improve in vivo longevity, and the indicator moiety may be oxidized even in the presence of a platinum layer having an increased surface area. In some embodiments, the present invention provides broader protection against various degradative species and increases longevity of partially or fully implantable devices.

In some embodiments, the sensor 100 may include a multiple metal protective system that includes multiple protective metals. In some embodiments, the multiple metals may interact and/or react with degradative species. In some embodiments, the multiple metals may neutralize degradative species. In some embodiments, the multiple metals may bind to degradative species. In some embodiments, the multiple metals may sequester degradative species so as to inhibit, reduce, and/or prevent degradation of the indicator molecules 104 of the analyte indicator 106 caused by the degradative species. Accordingly, in some embodiments, the multiple metals may reduce deterioration of the analyte indicator 106. In some non-limiting embodiments, the multiple metals may include one or more phenylboronic acid compounds that interact with degradative species without compromising signal integrity or performance of the sensor.

In some non-limiting embodiments, a sensor 100 for measurement of an analyte (e.g., glucose) in a medium (e.g., interstitial fluid) within a living animal (e.g., a human) may include a sensor housing 102 and an analyte indicator 106. In some embodiments, the analyte indicator may include one or more indicator molecules 104, which may be distributed throughout the analyte indicator 106. In some embodiments, the indicator molecules 104 may be configured to reversibly bind the analyte. In some embodiments, the analyte indicator 106 may cover at least a portion of the sensor housing 102. In some embodiments, the sensor 100 may include a light source 108 (e.g., within the sensor housing 102) configured to emit excitation light 329. In some embodiments, the indicator molecules 104 may configured to be irradiated by the excitation light 329 and emit light 331 indicative of the amount of the analyte in the medium within the living animal. In some embodiments, the sensor 100 may include a photodetector 224 (e.g., within the sensor housing 102) that is sensitive to light 331 emitted by the one or more indicator molecules 104 and configured to generate a signal indicative of the amount of the analyte in the medium within the living animal.

In some embodiments, the sensor 100 may include a multiple metal protective system that includes multiple protective metals. In some embodiments, the multiple metals may interact with multiple degradative species. In some embodiments, the multiple metal protective system may protect indicator molecules 104 of the analyte indicator 106 by preventing or reducing degradation or interference caused by degradative species or biological oxidizers. In some embodiments, the multiple metal protective system may protect the indicator molecules 104 without compromising signal integrity or performance of the sensor 100. In some non-limiting embodiments, the sensor 100 may include a drug eluting matrix and/or a layer of catalyst provided on or incorporated in the analyte indicator 106.

Figure 4A:
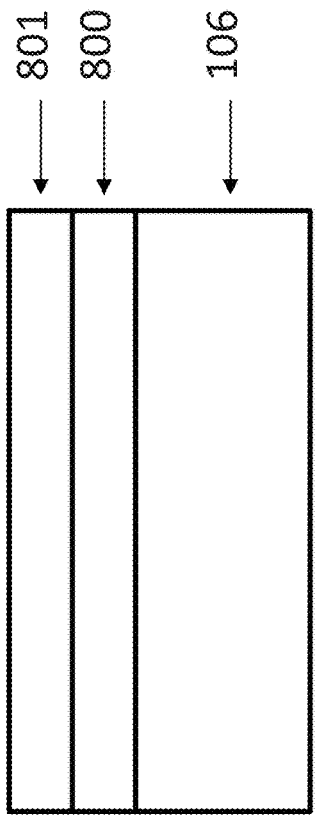
FIGS. 4A and 4B are schematic views illustrating an analyte indicator and protective layers embodying aspects of the present invention.
Figure 4B:
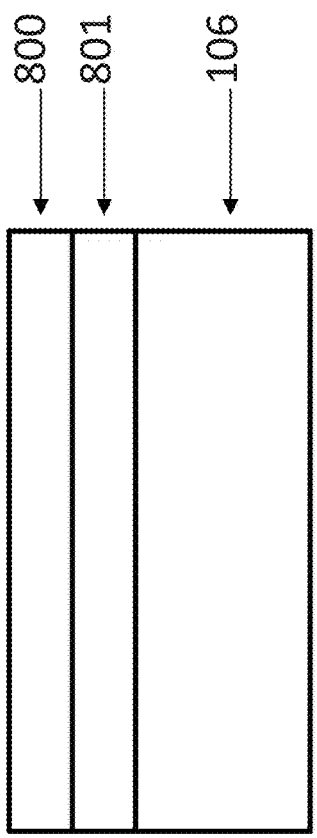

In some non-limiting embodiments, as shown in FIGS. 4A-5B, the multiple metal protective system may include a first metal layer 800 and a second metal layer 801. In some non-limiting embodiments, a sensor 100 may include a sensor housing 102, and an analyte indicator 106 covering at least a portion of the sensor housing 102. In some embodiments, as shown in FIG. 4A, the first metal layer 800 may cover at least a portion of the analyte indicator 106, and the second metal layer 801 may cover at least a portion of the first metal layer 800. In some non-limiting alternative embodiments, as shown in FIG. 4B, the second metal layer 801 may cover at least a portion of the analyte indicator 106, and the first metal layer 800 may cover at least a portion of the second metal layer 801.

Figure 5A:
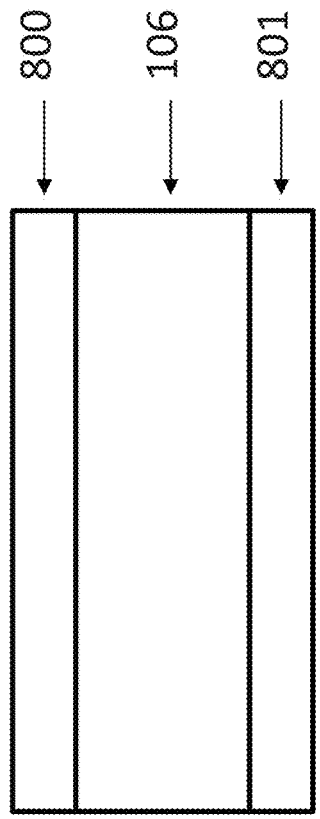
FIGS. 5A and 5B are schematic views illustrating an analyte indicator and protective layers embodying aspects of the present invention.
Figure 5B:
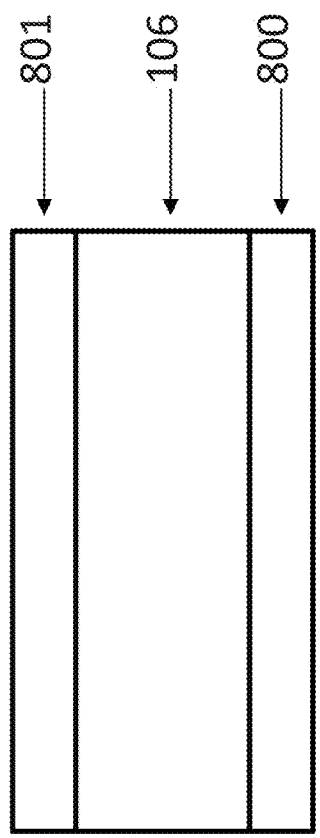

In some non-limiting embodiments, as illustrated in FIGS. 5A and 5B, the first metal layer 800 may be applied to a first surface of an analyte indicator 106, the second metal layer 801 may be applied to a second surface of the analyte indicator 106, and the second surface may be a different surface of the analyte indicator 106 than the first surface. For example, in some non-limiting embodiments, as shown in FIG. 5A, the first metal layer 800 may cover at least a portion of a first surface of the analyte indicator 106, the second metal layer 801 may cover at least a portion of a second surface of the analyte indicator 106, and the second surface may be on a side of the analyte indicator 106 opposite to the first surface. In some embodiments, the second metal layer 801 may be provided between the sensor housing 102 and the analyte indicator 106. For another example, in some non-limiting embodiments, as shown in FIG. 5B, the second metal layer 801 may cover at least a portion of the first surface of the analyte indicator 106, and the first metal layer 800 may cover at least a portion of the second surface of the analyte indicator 106. In some embodiments, the first metal layer 800 may be provided between the sensor housing 102 and the analyte indicator 106.

In some non-limiting embodiments, the first metal layer 800 may include a first metal selected from Cu, W, Pt, Fe, Mo, Co, and oxides, alloys, and complexes of those metals (e.g., alloys such as Pt/Rh and Pt/Lr). In some non-limiting embodiments, the first metal layer 800 may include the first metal and one or more additional metals selected from Cu, W, Pt, Fe, Mo, Co, and oxides, alloys, and complexes of those metals. In some non-limiting embodiments, the second metal layer 801 may include a second metal selected from Mo, W, Cu, Fe, Co, and oxides, alloys, and complexes of those metals. In some non-limiting embodiments, the second metal layer 801 may include the second metal and one or more additional metals selected from Mo, W, Cu, Fe, Co, and oxides, alloys, and complexes of those metals. In some embodiments, the first metal and the second metal may be different metals. In some non-limiting embodiments, the first metal may be platinum, and the second metal may be molybdenum. In some non-limiting embodiments, the first metal may be copper, and the second metal may be molybdenum. In some non-limiting alternative embodiments, the first metal may be platinum, and the second metal may be tungsten. In some other non-limiting alternative embodiments, the first metal may be tungsten, and the second metal may be molybdenum. In some other non-limiting alternative embodiments, the first metal layer 800 includes platinum and the second metal layer 801 includes tungsten.

Figure 6A:
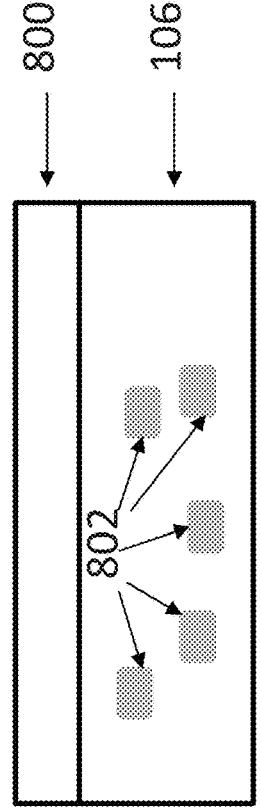
FIGS. 6A and 6B are schematic views illustrating an analyte indicator, a protective layer, and a protective material embodying aspects of the present invention.
Figure 6B:
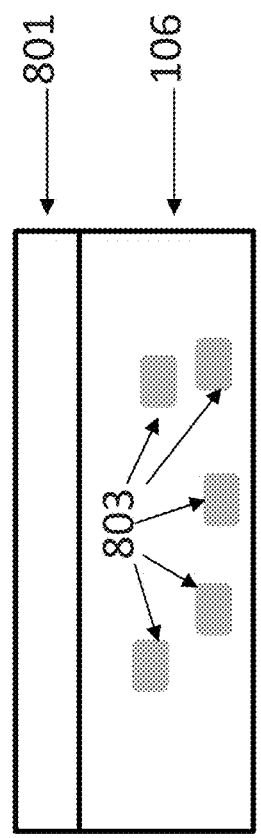
Figure 10A:
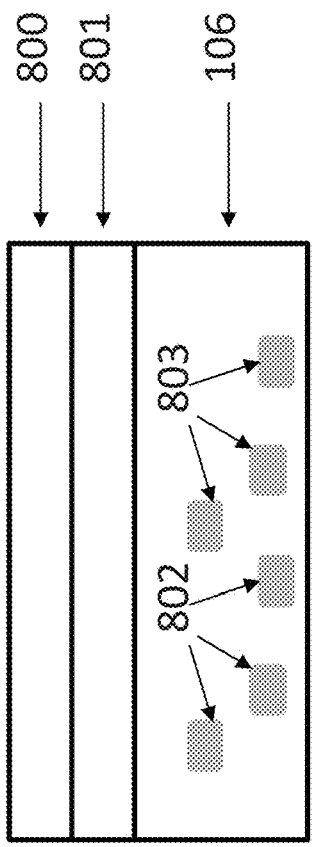
FIGS. 10A and 10B are schematic views illustrating an analyte indicator, protective layers, and protective materials embodying aspects of the present invention.
Figure 10B:
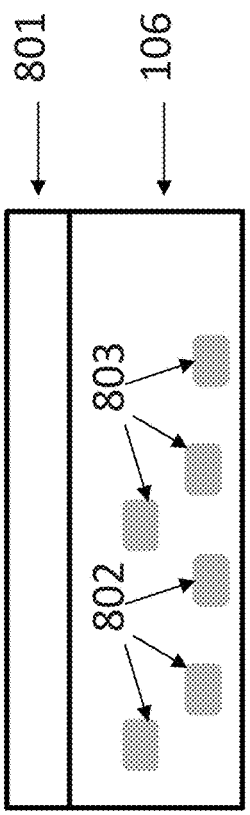
Figure 11A:
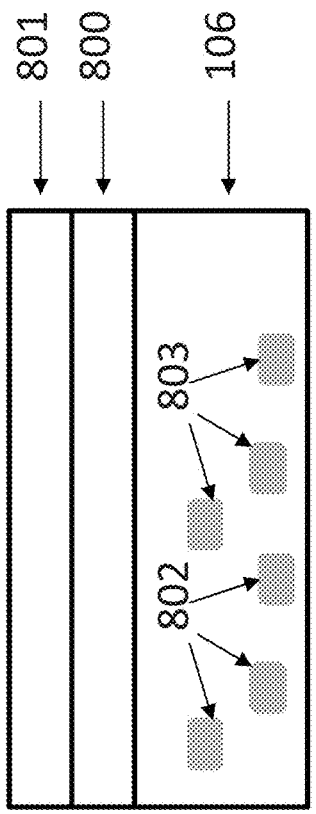
FIGS. 11A and 11B are schematic views illustrating an analyte indicator, a protective layer, and protective materials embodying aspects of the present invention.
Figure 11B:
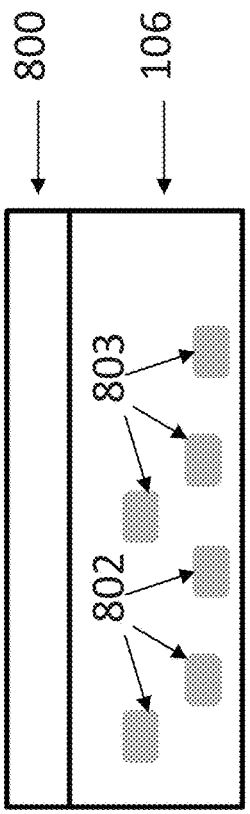

In some non-limiting embodiments, as shown in FIGS. 6A-11B, the multiple metal protective system may include (i) one or more metal layers on or in proximity to the analyte indicator 106 and (ii) metal particles of one or more metals incorporated into the analyte indicator 106. In some non-limiting embodiments, as shown in FIGS. 6A and 11A, the multiple metal protective system may include the first metal layer 800 and first metal particles 802. In some embodiments, the first metal layer 800 may cover a portion of the analyte indicator 106, and the first metal particles 802 may be incorporated in the analyte indicator 106. In some embodiments, the first metal layer 800 may include at least the first metal (e.g., the metal selected from Cu, W, Pt, Fe, Mo, Co, and oxides, alloys, and complexes of those metals), the first metal particles 802 may include at least the second metal (e.g., the metal selected from Mo, W, Cu, Fe, Co, and oxides, alloys, and complexes of those metals), and the first and second metals may be different metals. In some non-limiting alternative embodiments, as shown in FIGS. 6B and 11B, the multiple metal protective system may include the second metal layer 801 and second metal particles 803. In some embodiments, the second metal layer 801 may cover at least a portion of the analyte indicator 106, and the second metal particles 803 may be incorporated in the analyte indicator 106. In some embodiments, the second metal layer 801 may include at least the second metal, the second metal particles 803 may include at least the first metal, and the first and second metals may be different metals.

In some non-limiting embodiments, as shown in FIGS. 11A and 11B, the multiple metal protective system may include one of the first and second metal layers 800 and 801 and both of the first and second metal particles 802 and 803. For example, in some non-limiting embodiments, as shown in FIG. 11A, the multiple metal protective system may include the first metal layer 800, the first metal particles 802, and the second metal particles 803. In some non-limiting embodiments, the first metal layer 800 and the second metal particles 803 may each include at least a first metal (e.g., a metal selected from Cu, W, Pt, Fe, Mo, Co, and oxides, alloys, and complexes of those metals). In some non-limiting embodiments, the first metal layer 800 and the second metal particles 803 may include at least the same first metal, but this is not required, and, in some non-limiting alternative embodiments, the first metal layer 800 and the second metal particles 803 may include different metals selected from Mo, W, Cu, Fe, Co, and oxides, alloys, and complexes of those metals. In some non-limiting embodiments, the first metal particles 802 may include at least the second metal (e.g., the metal selected from Mo, W, Cu, Fe, Co, and oxides, alloys, and complexes of those metals), and the second metal may be different than the one or more first metals selected for the first metal layer 800 and the second metal particles 803.

For another example, in some non-limiting embodiments, as shown in FIG. 11B, the multiple metal protective system may include the second metal layer 801, the first metal particles 802, and the second metal particles 803. In some non-limiting embodiments, the second metal layer 801 and the first metal particles 802 may each include at least a second metal (e.g., a metal selected from Mo, W, Cu, Fe, Co, and oxides, alloys, and complexes of those metals). In some non-limiting embodiments, the second metal layer 801 and the first metal particles 802 may include at least the same second metal, but this is not required, and, in some non-limiting alternative embodiments, the second metal layer 801 and the first metal particles 802 may include different metals selected from Mo, W, Cu, Fe, Co, and oxides, alloys, and complexes of those metals. In some non-limiting embodiments, the second metal particles 803 may include at least the first metal (e.g., the metal selected from Cu, W, Pt, Fe, Mo, Co, and oxides, alloys, and complexes of those metals), and the first metal may be different than the one or more second metals selected for the second metal layer 801 and the first metal particles 802.

In some non-limiting embodiments, as shown in FIGS. 7A-10B, the multiple metal protective system may include a first metal layer 800, a second metal layer 801, and metal particles of one or more metals incorporated into the analyte indicator 106. In some embodiments, as shown in FIGS. 7A, 7B, 10A, and 10B, one of the first and second metal layers 800 and 801 may cover at least a portion of the analyte indicator 106, and the other of the first and second metal layers 800 and 801 may cover at least a portion of the one of the first and second metal layers 800 and 801 (see description of FIGS. 4A and 4B above). In some alternative embodiments, as shown in FIGS. 8A-9B, one of the first and second metal layers 800 and 801 may be applied to a first surface of an analyte indicator 106, the other of the first and second metal layer 800 and 801 may be applied to a second surface of the analyte indicator 106, and the second surface may be a different surface of the analyte indicator 106 than the first surface (see description of FIGS. 5A and 5B above). In some embodiments, as shown in FIGS. 7A-10B, the multiple metal protective system may include one or more of the first and second metal particles 802 and 803 in addition to the first and second metal layers 800 and 801.

In some non-limiting embodiments, as shown in FIGS. 9A-10B, the multiple metal protective system may include both of the first and second metal particles 802 and 803 in addition to the first and second metal layers 800 and 801 (see description of FIGS. 11A-11B above). In some non-limiting embodiments, the first metal layer 800 and the second metal particles 803 may each include at least a first metal (e.g., a metal selected from Cu, W, Pt, Fe, Mo, Co, and oxides, alloys, and complexes of those metals). In some non-limiting embodiments, the first metal layer 800 and the second metal particles 803 may include at least the same first metal, but this is not required, and, in some non-limiting alternative embodiments, the first metal layer 800 and the second metal particles 803 may include different metals selected from Cu, W, Pt, Fe, Mo, Co, and oxides, alloys, and complexes of those metals. In some non-limiting embodiments, the second metal layer 801 and the first metal particles 802 may each include at least a second metal (e.g., a metal selected from Mo, W, Cu, Fe, Co, and oxides, alloys, and complexes of those metals). In some non-limiting embodiments, the second metal layer 801 and the first metal particles 802 may include at least the same second metal, but this is not required, and, in some non-limiting alternative embodiments, the second metal layer 801 and the first metal particles 802 may include different metals selected from Mo, W, Cu, Fe, Co, and oxides, alloys, and complexes of those metals. In some non-limiting embodiments, one or more (e.g., all) of the metals of the first metal layer 800, second metal layer 801, first metal particles 802, and second metal particles 803 may be different.

Figure 12:
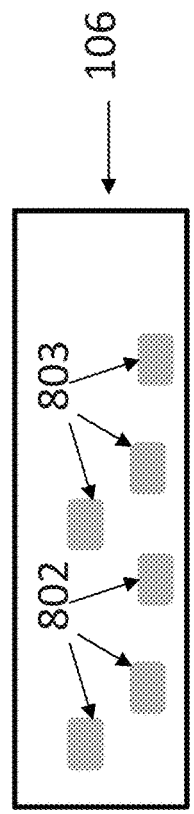
FIG. 12 is a schematic view illustrating an analyte indicator and protective materials embodying aspects of the present invention.

In some non-limiting alternative embodiments, as shown in FIG. 12, the multiple metal protective system need not include a metal layer on a surface of the analyte indicator. For example, as shown in FIG. 12, in some embodiments, the multiple metal protective system may include the first metal particles 802 and second metal particles 803, which may be incorporated in the analyte indicator 106. In some embodiments, the first metal particles 802 may include at least the second metal (e.g., the metal selected from Mo, W, Cu, Fe, Co, and oxides, alloys, and complexes of those metals), the second metal particles 803 may include at least a first metal (e.g., a metal selected from Cu, W, Pt, Fe, Mo, Co, and oxides, alloys, and complexes of those metals), and the first and second metals may be different metals.

Figure 14B:
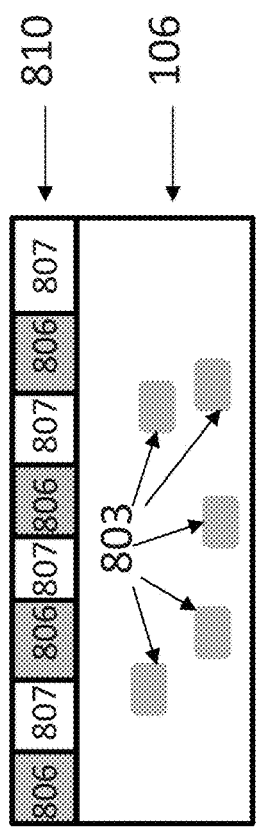
FIGS. 14A and 14B are schematic views illustrating an analyte indicator, a protective layer, and a protective material embodying aspects of the present invention.
Figure 13:
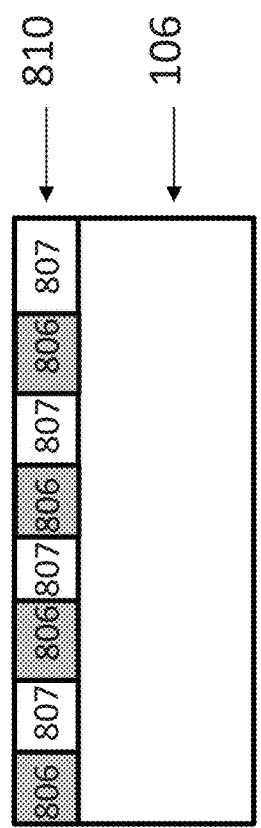
FIG. 13 is a schematic view illustrating an analyte indicator and a protective layer embodying aspects of the present invention.

As noted above, in some embodiments, a sensor 100 may include a sensor housing 102, an analyte indicator 106 that covers at least a portion of the sensor housing 102, and a multiple metal protective system. In some non-limiting embodiments, as shown in FIGS. 13-15, the multiple metal protective system may include a multi-metal layer 810 covers at least a portion of the analyte indicator 106. In some embodiments, as shown in FIGS. 13-15, the multi-metal layer 810 may include at least a first metal 806 and a second metal 807. In some embodiments, the first metal 806 may be selected from Cu, W, Pt, Fe, Mo, Co, and oxides, alloys, and complexes of those metals. In some embodiments, the second metal 807 may be selected from Mo, W, Cu, Fe, Co, and oxides, alloys, and complexes of those metals. In some embodiments, the first metal 806 and the second metal 807 may be different metals.

Figure 14A:
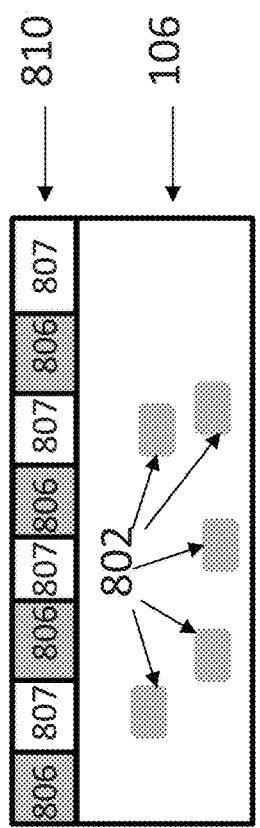
Figure 15:
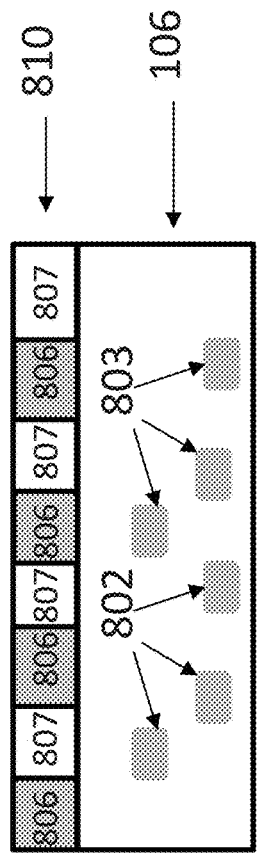
FIG. 15 is a schematic view illustrating an analyte indicator, a protective layer, and protective materials embodying aspects of the present invention.

In some embodiments, as shown in FIGS. 14A-15, the multiple metal protective system may include the multi-metal layer 810 and one or more of the first and second metal particles 802 and 803. In some non-limiting embodiments, the first metal 806 and the second metal particles 803 may include at least the same metal, but this is not required, and, in some non-limiting alternative embodiments, the first metal 806 and the second metal particles 803 may include different metals selected from Cu, W, Pt, Fe, Mo, Co, and oxides, alloys, and complexes of those metals. In some non-limiting embodiments, the second metal 807 and the first metal particles 802 may include at least the same metal, but this is not required, and, in some non-limiting alternative embodiments, the second metal 807 and the first metal particles 802 may include different metals selected from Mo, W, Cu, Fe, Co, and oxides, alloys, and complexes of those metals. In some non-limiting embodiments, one or more (e.g., all) of the metals of the first metal layer 800, second metal layer 801, first metal particles 802, and second metal particles 803 may be different.

Figure 16B:
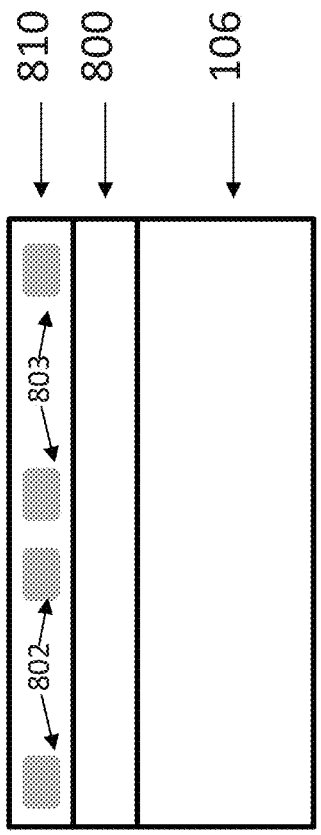
FIG. 16B is a schematic view illustrating an analyte indicator, a first metal layer, and a carrier material having first and second metals incorporated therein embodying aspects of the present invention.
Figure 16A:
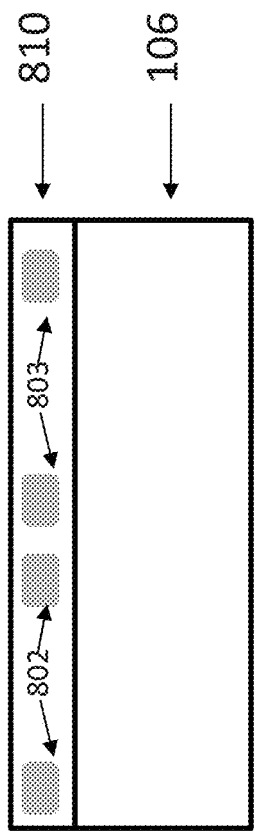
FIG. 16A is a schematic view illustrating an analyte indicator, and a carrier material having first and second metals incorporated therein embodying aspects of the present invention.
Figure 16C:
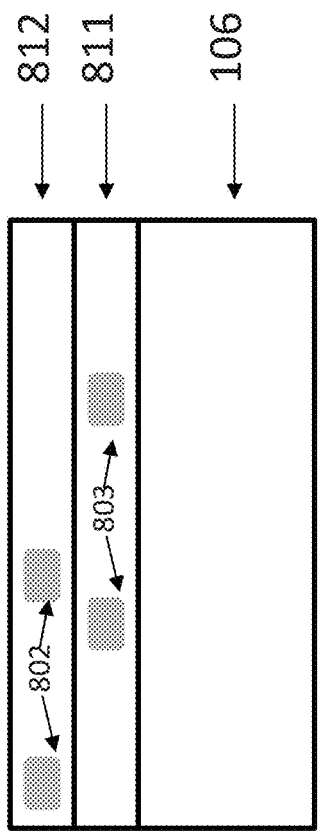
FIG. 16C is a schematic view illustrating an analyte indicator, a first carrier material having a metal incorporated therein, and a second carrier material having a different metal incorporated therein embodying aspects of the present invention.

In some embodiments, as shown in FIGS. 16A-C, the sensor device may include one or more carrier materials 810 and 811. In some embodiments, the one or more carrier materials may be independently a membrane, mesh, nylon, fabric, matrix, sponge, or other pore-containing material covering at least a portion of the analyte indicator 106. In some embodiments, first and second metal particles 802 and 803 may be incorporated within the carrier material 810 covering the analyte indicator 106 as shown in FIG. 16A. In some embodiments, first and second metal particles 802 and 803 may be incorporated within the carrier material 810 covering a first metal layer 800 that covers the analyte indicator 106 as shown in FIG. 16B. Additional metal layers may also be provided between the carrier material 810 and the first metal layer 800 (not shown). In some embodiments, metal particles 802 may be incorporated into a first carrier material 811 and different metal particles 803 may be incorporated into a second carrier material 812, wherein the first carrier material 811 covers the analyte indicator 106 as shown in FIG. 16C. Additional metal layers may also be provided between the first carrier material 811 and the indicator 106 and/or between the first carrier material 811 and the second carrier material 812 (not shown).

In some embodiments, a fully or partially implantable sensor 100 including a multiple metal protective system may have improved performance over a sensor that does not include a multiple metal protective system. For instance, in some non-limiting embodiments, the multiple metal protective system may improve the longevity and functionality of the sensor 100.

In some embodiments, a multiple metal protective system may improve protection against degradative species. Assays with a series of 1 cm×1 cm metal foils were conducted and the results are reported in Tables 1 and 2. In an assay, protective activities listed in Table 1 were found against hydrogen peroxide.

TABLE 1

| Metal(s) | $H_2O_2$ assay<br>Reaction rate (k) $(min^{-1})$ |
|---|---|
| Cu | 0.0157 |
| W | 0.0150 |
| Pt | 0.0120 |
| Fe | 0.0115 |
| Mo | 0.0112 |
| Co | 0.0046 |
| Pt/Rh (alloy) | 0.0033 |
| Pt/Ir (alloy) | 0.0032 |
| Au, Pd, Ni, Ta, Mg | No activity |

Unexpectedly, Au, Pd, Ni, Ta, Mg had no detectable activity against hydrogen peroxide.

In an assay, protective activities listed in Table 2 were found against hypochlorite.

TABLE 2

| Metal(s) | Hypochlorite assay<br>Reaction rate (k) $(min^{-1})$ |
|---|---|
| Mo | 0.0052 |
| W | 0.0044 |
| Cu | 0.0041 |
| Fe | 0.0029 |
| Co | 0.0015 |
| Au, Pd, Ni, Ta, Mg,<br>Pt, Pt/Rh, Pt/Ir | No activity |

The results demonstrate that, for example and without limitation, platinum can be used to degrade hydrogen peroxide but is not useful to degrade hypochlorite. The results also demonstrate that, for example and without limitation, copper was found to be more reactive than molybdenum against hydrogen peroxide but less reactive than molybdenum against hypochlorite. Unexpectedly, Au, Pd, Ni, Ta, Mg, Pt, Pt/Rh, Pt/Ir had no detectable activity against hypochlorite.

In some embodiments, the multiple metals (e.g., in one or more metal layers on the analyte indicator 106 and/or one or more metal particles incorporated in the analyte indicator 106) in the multiple metal protective system may improve protection against degradative species because one of the metals may degrade one type of degradative species (e.g., hydrogen peroxide) and another one of the metals may degrade another type of degradative species (e.g., hypochlorite).

In some embodiments, the multiple metals (e.g., in one or more metal layers on the analyte indicator 106 and/or one or more metal particles incorporated in the analyte indicator 106) in the multiple metal protective system may additionally or alternatively improve protection against degradative species because one metal layer (e.g., the first metal layer 800) may act to promote adhesion of another metal layer (e.g., the second metal layer 801). For example, molybdenum may adhere better to platinum than to an analyte indicator 106, which may be, for example and without limitation, a glucose indicating hydrogel than molybdenum. For instance, in the embodiments shown in FIGS. 4A, 7A, and 10A, the multiple metal protective system may include a first metal layer 800 applied to at least a portion of the analyte indicator 106 and a second metal layer 801 applied to at least a portion of the first metal layer 800, and the first and second metal layers 800 and 801 may include first and second metals (e.g., platinum and molybdenum), respectively. In some embodiments, the first metal (e.g., platinum) of the first metal layer 800 may promote adhesion of the second metal of the second metal layer 801. That is, the second metal layer 801 may adhere better to the first metal layer 800 than the second metal layer 801 would adhere to the analyte indicator 106 if applied directly to the analyte indicator 106. Accordingly, the multiple metals of the multiple metal protective system may allow the system to include a metal that could not be used if only one metal were used. In some non-limiting embodiments, the multiple metal protective system may include a Pt layer covered by a Mo layer, which may enable improved adhesion to the hydrogel and improve catalysis against both hydrogen peroxide and hypochlorite.

Examples

A non-limiting example of a sensor ("Example Sensor 1") includes a sensor housing, a hydrogel on at least a portion of the sensor housing, indicator molecules contained in the hydrogel, and Pt sputtered on at least a portion of the hydrogel, and has a useful life of 90 days implanted in a human patient.

A non-limiting example of a sensor ("Example Sensor 2") that is the same as Example Sensor 1 but is further protected by a Mo layer provided over the Pt has a useful life of at least 180 days when it is implanted in a human patient.

A non-limiting example of a sensor ("Example Sensor 3") that is the same as Example Sensor 1 but is further protected by Cu sputtered in combination with the Pt on the hydrogel has a useful life of at least 180 days when it is implanted in a human patient.

A non-limiting example of a sensor ("Example Sensor 4") that is the same as Example Sensor 1 but is further protected by Cu that is sputtered in combination with the Pt on the hydrogel and has a Mo layer over the co-sputtered Pt/Cu has a useful life of at least 270 days when it is implanted in a human patient.

A non-limiting example of a sensor ("Example Sensor 5") that is the same as Example Sensor 1 but is further protected by Cu that is incorporated in the hydrogel has a useful life of at least 180 days when it is implanted in a human patient.

A non-limiting example of a sensor ("Example Sensor 6") that is the same as Example Sensor 1 but is further protected by Cu incorporated in the hydrogel and a Mo layer provided over the Pt has a useful life of at least 270 days when it is implanted in a human patient.

A non-limiting example of a sensor ("Example Sensor 7") that is the same as Example Sensor 1 but is further protected by Pt and Cu incorporated in the hydrogel and a W layer over the Pt has a useful life of at least 270 days when it is implanted in a human patient.

A non-limiting example of a sensor ("Example Sensor 8") that is the same as Example Sensor 1 but is further protected by Pt, Cu, and Mo incorporated in the hydrogel and a W layer over the Pt has a useful life of at least 300 days when it is implanted in a human patient.

A non-limiting example of a sensor ("Example Sensor 9") that is the same as Example Sensor 1 but is further protected by Pt, Cu, and W incorporated in the hydrogel and a Mo layer over the Pt has a useful life of at least 300 days when it is implanted in a human patient.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention. For example, although in some embodiments, the analyte sensor 100 may be an optical sensor, this is not required, and, in one or more alternative embodiments, the analyte sensor may be a different type of analyte sensor, such as, for example, an electrochemical sensor, a diffusion sensor, or a pressure sensor. Also, although in some embodiments, the analyte sensor 100 may be an implantable sensor, this is not required, and, in some alternative embodiments, the analyte sensor may be a transcutaneous sensor having a wired connection to an external transceiver. For example, in some alternative embodiments, the analyte sensor 100 may be located in or on a transcutaneous needle (e.g., at the tip thereof). In these embodiments, instead of wirelessly communication using an antenna (e.g., inductive element 114), the analyte sensor may communicate with the external transceiver using one or more wires connected between the external transceiver and a transceiver transcutaneous needle including the analyte sensor. For another example, in some alternative embodiments, the analyte sensor may be located in a catheter (e.g., for intravenous blood glucose monitoring) and may communicate (wirelessly or using wires) with an external transceiver.

What is claimed is:

1. A sensor for measurement of an analyte in a medium within a living animal, the sensor comprising:
   a sensor housing;
   an analyte indicator covering at least a portion of the sensor housing; and
   a protective system including multiple metals incorporated in and/or in close proximity to a surface of the analyte indicator, and the multiple metals are configured to reduce deterioration of the analyte indicator;
   wherein the protective system includes first and second metal layers, the first metal layer covers at least a portion of the analyte indicator and includes a first metal of the multiple metals, the second metal layer covers at least a portion of the first metal layer and includes a second metal of the multiple metals, the first and second metals are different, and the second metal layer is capable of adhering to the first metal layer to a greater extent than an extent to which the second metal layer is capable of adhering to the analyte indicator.

2. The sensor of claim 1, wherein the protective system further comprises metal particles incorporated within the analyte indicator, and the metal particles include one or more of the multiple metals.

3. The sensor of claim 2, wherein the metal particles include two or more of the multiple metals.

4. The sensor of claim 1, wherein the first metal layer is a multi-metal layer comprising two or more of the multiple metals.

5. The sensor of claim 1, wherein the multiple metals are configured to collectively interact or react with multiple degradative species.

6. The sensor of claim 1, wherein the multiple metals of the protective system are configured to collectively interact or react with at least two of hydrogen peroxide, a reactive oxygen species, enzymes, metal ions, a reactive nitrogen species, and a free radical.

7. The sensor of claim 1, wherein the multiple metals of the protective system are configured to inhibit oxidative properties of degradative species.

8. The sensor of claim 1, wherein the first metal is selected from Cu, W, Pt, Fe, Mo, oxides, alloys, and complexes thereof, the second metal is selected from Mo, W, Cu, Fe, and Co, oxides, alloys, and complexes thereof.

9. The sensor of claim 1, wherein the first metal is Pt, and the second metal is Mo.

10. The sensor of claim 1, wherein the first metal is Cu, and the second metal is Mo.

11. The sensor of claim 1, further comprising:
 a radiation source contained in said sensor housing and configured to emit radiation to the analyte indicator; and
 a photosensitive element contained in the sensor housing and configured to receive light emitted by the analyte indicator.

12. The sensor of claim 1, comprising a carrier material covering at least a portion of the analyte indicator, wherein the multiple metals are incorporated within the carrier material.

13. The sensor of claim 12, wherein the carrier material is a membrane, mesh, nylon, fabric, matrix, sponge or other pore-containing material.

14. A method for detecting the presence or concentration of an analyte in an in vivo sample comprising:
 exposing the in vivo sample to a device having a detectable quality that changes when the device is exposed to an analyte of interest, wherein the device comprises:
  a sensor housing;
  an analyte indicator covering at least a portion of the sensor housing; and
  a protective system including multiple metals incorporated in and/or in close proximity to a surface of the analyte indicator, and the multiple metals are configured to reduce deterioration of the analyte indicator;
 wherein the protective system includes first and second metal layers, the first metal layer covers at least a portion of the analyte indicator and includes a first metal of the multiple metals, the second metal layer covers at least a portion of the first metal layer and includes a second metal of the multiple metals, the first and second metals are different, and the second metal layer is capable of adhering to the first metal layer to a greater extent than an extent to which the second metal layer is capable of adhering to the analyte indicator; and
 measuring a change in the detectable quality to thereby detect the presence or concentration of the analyte in the in vivo sample.

15. A sensor for measurement of an analyte in a medium within a living animal, the sensor comprising:
 a sensor housing;
 an analyte indicator covering at least a portion of the sensor housing, wherein the analyte indicator comprises indicator molecules, and the indicator molecules are configured to reversibly bind the analyte; and
 a protective system including multiple metals incorporated in and/or in close proximity to a surface of the analyte indicator, and the multiple metals are configured to reduce deterioration of the analyte indicator;
 wherein the protective system includes first and second metal layers, the first metal layer covers at least a portion of the analyte indicator and includes a first metal of the multiple metals, the second metal layer covers at least a portion of the first metal layer and includes a second metal of the multiple metals, the first metal is Pt, and the second metal is Mo.

* * * * *